United States Patent [19]

Son et al.

[11] Patent Number: 4,675,353
[45] Date of Patent: Jun. 23, 1987

[54] HINDERED 2-KETO-1,4-DIAZACYCLOALKANE OLIGOMERS CONTAINING TRIAZINE RINGS AND COMPOSITIONS STABILIZED THEREBY

[75] Inventors: Pyong-Nae Son, Akron; John T. Lai, Broadview Heights, both of Ohio

[73] Assignee: The BFGoodrich Company, Akron, Ohio

[21] Appl. No.: 696,133

[22] Filed: Jan. 29, 1985

[51] Int. Cl.$^4$ .............................................. C08K 5/34
[52] U.S. Cl. ..................................... 524/96; 524/100; 544/113; 544/219; 544/231; 544/384; 544/401; 252/401
[58] Field of Search .................. 524/96, 100; 544/113, 544/219, 231, 384; 252/401

[56] References Cited
U.S. PATENT DOCUMENTS

| | | | |
|---|---|---|---|
| 4,108,829 | 8/1978 | Cassandrini et al. | 524/100 |
| 4,190,571 | 2/1980 | Lai et al. | 524/98 |
| 4,412,020 | 10/1983 | Loffelman et al. | 524/100 |
| 4,426,472 | 1/1984 | Berner | 524/100 |
| 4,455,401 | 6/1984 | Son et al. | 524/100 |
| 4,504,610 | 3/1985 | Fontanelli et al. | 524/100 |
| 4,547,538 | 10/1985 | Lai et al. | 524/100 |
| 4,629,752 | 12/1986 | Layer et al. | 524/100 |

Primary Examiner—John Kight
Assistant Examiner—Kriellion Morgan
Attorney, Agent, or Firm—Alan A. Csontos; A. D. Lobo

[57] ABSTRACT

Novel hindered 2-keto-1,4-diazacycloalkane-triazine oligomers having the general formula

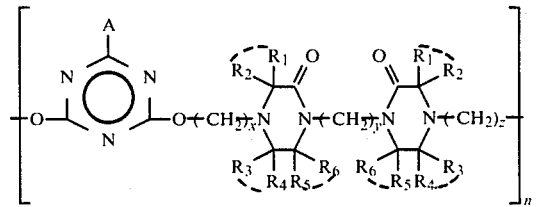

are useful antioxidants and UV stabilizers for various polymers.

5 Claims, No Drawings

HINDERED 2-KETO-1,4-DIAZACYCLOALKANE OLIGOMERS CONTAINING TRIAZINE RINGS AND COMPOSITIONS STABILIZED THEREBY

BACKGROUND OF THE INVENTION

Organic materials, both natural and synthetic, are conventionally protected against degradation by ultraviolet (UV) radiation by incorporating a UV light stabilizer in the material. Many classes of compounds are known to be useful UV light stabilizers, with some compounds being more effective than others. Particularly effective 2-keto-diazacycloalkanes, which provide stabilized compositions that are resistant to degradation by UV light, include the 2-keto-1,4-diazacycloalkanes disclosed in U.S. Pat. No. 4,190,571; and the 2-keto-1,5-diazacycloalkanes disclosed in U.S. Pat. No. 4,207,228. Other 2-keto-diazacycloalkanes useful as UV light stabilizers are disclosed in U.S. Pat. Nos. 3,919,234; 3,920,659; and 3,928,330 which teach substituted piperazinediones.

The compounds of this invention belong to a well-recognized chemical class of ultraviolet light stabilizers. Compounds of this class include piperidinyl-triazine derivatives such as those disclosed in U.S. Pat. Nos. 4,386,177; 4,356,287; 4,321,374; 4,294,963; 4,234,728 and 4,108,829. The above patents describe oligomers of triazine rings with monoaza-ring substituents, and teach the particular use of these oligomers as light stabilizers in polyolefins. The novel compounds of the present invention contain 2-keto-diaza rings in the oligomeric backbone which are bonded to the triazine rings through an ether linkage. The novel compounds of this invention are excellent stabilizers for polyolefins and exhibit resistance to solvent extraction.

It is an object of the present invention to provide novel 2-keto-1,4-diazacycloalkane-triazine oligomers which are useful as stabilizers for a variety of organic materials. It is a further object of this invention to provide novel 2-keto-diazacycloalkane-triazine oligomers which are useful both as UV stabilizers and as antioxidants for various polymers. It is an even further object of this invention to provide novel 2-keto-diazacycloalkane-triazine stabilizers and stabilized compositions which are resistant to solvent extraction.

SUMMARY OF THE INVENTION

Novel hindered 2-keto-1,4-diazacycloalkane-triazine oligomers are useful antioxidants and UV stabilizers for organic materials such as polyolefins. The novel keto-diazacycloalkane-triazine stabilizer compounds of this invention may be represented by the general formula

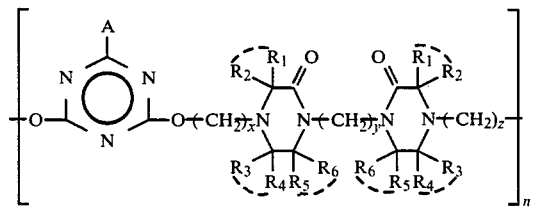

wherein
x, y, and z independently is an integer from 1 to about 10;
n ranges from 2 to about 20;
$R_1$, $R_2$, $R_3$ and $R_4$ each independently represent alkyl or haloalkyl having from 1 to about 12 carbon atoms, cyanoalkyl, aminoalkyl or iminoalkyl having from 2 to about 12 carbon atoms, cycloalkyl or hydroxy-cycloalkyl having from 5 to about 14 carbon atoms, alkenyl or aralkyl having from 7 to about 14 carbon atoms, alkylene having from 2 to about 7 carbon atoms, and $R_1$ and $R_2$ or $R_3$ and $R_4$ in combination with each other represent cycloalkyl having from 5 to about 14 carbon atoms; $R_5$ and $R_6$ are the same as $R_1$–$R_4$ hereinabove and additionally may be hydrogen; and A is piperidinyl, morpholinyl, alkylamino or dialkylamino having from 2 to about 12 carbon atoms.

DETAILED DESCRIPTION

This invention relates to novel hindered 2-keto-1,4-diazacycloalkane-triazine oligomers and stabilized compositions containing same. The novel keto-diazacycloalkane-triazines are useful as UV stabilizers and antioxidants for a variety of organic materials. They are particularly useful as UV light stabilizers in compositions subject to UV light degradation. As stabilizers they are used in the range from about 0.01 to about 10 parts by weight, and preferably from about 0.1 to about 1.0 part, per 100 parts by weight of organic material. These organic materials may be low or high molecular weight materials, and particularly include homopolymers, copolymers and mixtures thereof. Examples of materials that can be stabilized by the oligomers of this invention include oils; monomers, such as $\alpha,\beta$-olefinically unsaturated acrylates, dienes, vinyl nitriles and the like; alcohols; aldehydes; and natural and synthetic polymers. Examples of known polymeric materials which can be stabilized by the keto-diazacycloalkane-triazines of this invention include natural rubber, synthetic rubbers (such as cis-polyisoprene, styrene-butadiene rubber, dienenitrile rubbers), polyepihalohydrin polymers, polyurethanes, poly vinyl chloride resins, acrylonitrile-butadiene-styrene resins, polystyrene, polyacrylonitrile, polymethacryates, polycarbonates, varnish, phenol-formaldehyde resins, polyepoxides, polyesters, and polyolefin homo and copolymers such as polyethylene, polypropylene, ethylene-propylene polymers, ethylene-propylenediene polymers, ethylvinyl acetate polymers, and the like.

The novel 2-keto-1,4-diazacycloalkane-triazine oligomers of the present invention have the structural formula:

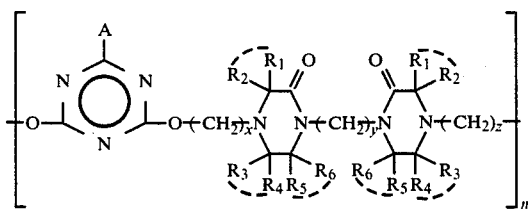

wherein
x, y, and z independently is an integer from 1 to about 10;
n ranges from 2 to about 20;
$R_1$, $R_2$, $R_3$ and $R_4$ each independently represent alkyl or haloalkyl having from 1 to about 12 carbon atoms, cyanoalkyl, aminoalkyl or iminoalkyl having from 2 to about 12 carbon atoms, cycloalkyl or hydroxy-cycloalkyl having from 5 to about 14 carbon atoms, alkenyl or aralkyl having from 7 to about 14 carbon atoms, alkylene having from 2 to about 7 carbon atoms, and $R_1$ and $R_2$ or $R_3$ and $R_4$ in combination with each other represent cycloalkyl having from 5 to about 14 carbon atoms; $R_5$ and $R_6$ are the same as $R_1$–$R_4$ hereinabove and additionally may be hydrogen; and A is piperidinyl, morpholinyl, dialkylamino or alkylamino having from 2 to about 12 carbon atoms. Preferably, $R_1$, $R_2$, $R_3$, and $R_4$ are methyl and $R_5$ and $R_6$ are hydrogen. Compounds falling within the scope of this invention include, for example, poly[oxy[6-(1,1,3,3-tetramethylbutyl)amino]-1,3,5-triazine-2,4-diyloxy-1,2-ethanediyl (2,2,6,6-tetramethyl-3-oxo-1,4-piperazinediyl)-1,2-ethanediyl(3,3,5,5-tetramethyl-2-oxo-1,4-piperazinediyl)-1,2-ethanediyl]; poly[oxy[6-(1-piperidinyl]-1,3,5-triazine-2,4-diyloxy-1,2-ethanediyl(2,2,6,6-tetramethyl-3-oxo-1,4-piperazine-diyl)-1,2-ethanediyl(3,3,5,5-tetramethyl-2-oxo-1,4-piperazinediyl)-1,2-ethanediyl]; and the like.

The novel compounds of this invention can be prepared by reaction of substituted 2-keto-1,4-diazacycloalkanes with substituted trazines in the presence of alkali metal. Suitable substituted 2-keto-1,4-diazacycloalkanes for use in this invention include those disclosed in U.S. Pat. No. 4,167,512, which is herein incorporated by reference. Suitable substituted triazines include the 1,3,5-triazines which are known in the art and particularly described in various U.S. patents, such as U.S. Pat. Nos. 4,356,287; 4,108,829; and 4,234,728, which are herein incorporated by reference. The reaction may be carried out in the presence of inert solvents such as chlorobenzene, acetone, dioxane, toluene, xylene and the like.

The novel keto-diazacycloalkane-triazine oligomers of this invention may be used to stabilize organic materials either alone or in combination with other secondary stabilizers. Particularly desirable secondary stabilizers are one or more antioxidants used in the range from about 0.1 part to about 20 parts by weight, preferably from about 0.1 part to about 5 parts by weight per 100 parts by weight of the material. Of the types of antioxidants to be used phenolic antioxidants are preferred. Most preferred are phenolic antioxidants such as 2,6-di-t-butyl-paracresol; 2,2'-methylene-bis-(6-t-butylphenol); 2,2'-thiobis-(4-methyl-6-t-butyl-phenol); 2,2'-methylene-bis-(6-t-butyl-4-ethyl-phenol); 4,4'-butylene-bis(6-t-butyl-m-cresol); 2-(4-hydroxy-3,5-di-t-butylanilino)-4,6-bis-(octylthio)-1,3,5-triazine; tris 2-[β-(3,5-di-tert-butyl-4-hydroxyphenyl)propionoxy]ethyl isocyanurate; tris-(3,5-di-t-butyl-4-hydroxybenzyl)isocyanurate; tetrakis[methylene(3,5-di-tert-butyl-4-hydroxyhydrocinnamate)]methane; tris 2-[β-(3,5-di-tert-butyl-4-hydroxyphenyl)propionoxy]ethyl isocyanurate; and other antioxidant synergists such as distearyl thiodipropionate; dilauryl thiodipropionate; tri(nonylphenyl)phosphite; and tin thioglycolate. Other ingredients such as lubricants, plasticizers, pigments, tackifiers, fillers, flame retardants, fungicides, and the like may also be added.

The substituted keto-diazacycloalkane-triazine stabilizers, and other compounding ingredients if used, can be admixed with organic materials using known mixing techniques and equipment such as internal mixing kettles, a Banbury mixer, a Henschel mixer, a two-roll mill, an extruder mixer, or other standard equipment, to yield a composition which may be extruded, pressed, blow-molded or the like into film, fiber or shaped articles. Usual mixing times and temperatures can be employed which may be determined with a little trial and error for any particular composition. The objective is to obtain intimate and uniform mixing of the components.

To further illustrate the present invention, the following specific examples are given, it being understood that this is merely intended in an illustrative and not a limitative sense.

EXAMPLE I

Preparation of poly[oxy[6-[1,1,3,3-tetramethylbutyl)amino]-1,3,5-triazine-2,4-diyloxy-1,2-ethanediyl(2,2,6,6-tetramethyl-3-oxo-1,4-piperazinediyl)-1,2-ethanediyl(3,3,5,5-tetramethyl-2-oxo-1,4-piperazine-diyl)-1,2-ethanediyl]

Into a 500 ml three-necked flask was placed 200 ml of dry xylenes and 4 drops of oleic acid. The above mixture was heated under a nitrogen blanket. When the temperature of the mixture reached 50° C., 0.92 grams of sodium metal was added. When the temperature of the mixture reached 105° C., 8.53 grams of 1,1'-(1,2-ethanediyl)bis[4-(2-hydroxyethyl)-3,3,5,5-tetramethylpiperazinone] was added over a 12 minute period. After refluxing overnight, 5.54 grams of 2,4-dichloro-6-(1,1,3,3-tetramethylbutyl)amino-1,3,5-triazine was added, and the mixture was refluxed for approximately 5 hours. About 50 ml of ethanol was added to the mixture and it was allowed to stir overnight at room temperature. The mixture was stripped to obtain a straw-colored solid, which was washed with 300 ml of water and isolated by filtration. After drying, 12.5 grams of solid product was obtained having a softening point range of 103°–116° C. and a number average molecular weight (Mn) of 1128. The product was identified as having the following structure

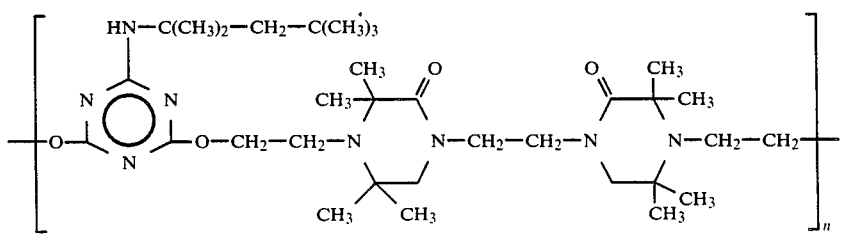

EXAMPLE II

Preparation of poly[oxy[6-(1-piperidinyl)-1,3,5-triazine-2,4-diyl]oxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl]

Into a 2-neck 100 ml flask, equipped with magnetic stirrer, condenser, and a Dean-Stark trap, were placed 8.53 grams of 1,1'-(1,2-ethanediyl)bis[4-(2-hydroxyethyl)-3,3,5,5-tetramethylpiperazinone], 4.66 grams of 2,4-dichloro-6-(1-piperidinyl)-1,3,5-triazine, 50 ml of chlorobenzene, and 1.68 grams of sodium hydroxide in 5 ml of water. The above mixture was heated to reflux and about 5.5 ml of water was collected. After refluxing overnight the reaction was terminated and the mixture cooled. After stripping, a solid product was obtained which was washed with 150 ml of water and isolated by filtration. The product was dried to yield 11.0 grams of a white solid having a softening point of about 115° C. and Mn 1341. The product was identified as having the following structure

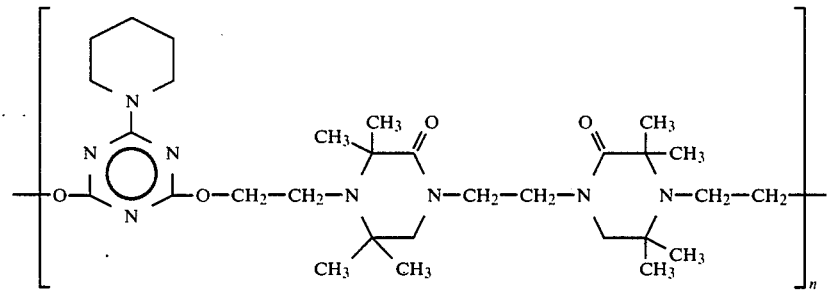

EXAMPLE III

The compounds prepared above were tested for their effectiveness as UV stabilizers in 2 mil (0.0254 mm) polypropylene strips. In each sample 0.05 parts by weight of tris 2-[β-(3,5-di-tert-butyl-4-hydroxyphenyl)-propionoxyoxy]ethyl isocyanurate per 100 parts by weight polypropylene was added as a secondary stabilizer. The samples were placed in a Xenon Weatherometer and the time period (failure time) measured for loss of 50% of original tensile strength. The results are presented in Table I below:

TABLE I

| Sample | UV Stabilizer (pbw) | Failure Time (hours) |
|---|---|---|
| Control | None | 260 |
| Example I | 0.1 | 770 |
| Example II | 0.1 | 820 |

(pbw is parts by weight)

The above results demonstrate the effectiveness of the compounds of this invention as UV stabilizers, particularly as synergist for conventional polymer stabilizers.

We claim:

1. A stabilized composition of matter comprising an organic material subject to ultraviolet light degradation having dispersed therein from about 0.01 part to about 10 parts by weight, per 100 parts by weight of said organic material, of a stabilizer compound of the formula:

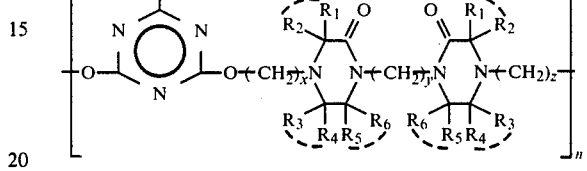

wherein x, y, and z independently is an integer from 1 to about 10;

n ranges from 2 to about 20;

$R_1$, $R_2$, $R_3$ and $R_4$ each independently represent alkyl or haloalkyl having from 1 to about 12 carbon atoms, cyanoalkyl, aminoalkyl or iminoalkyl having from 2 to about 12 carbon atoms, cycloalkyl or hydroxy-cycloalkyl having from 5 to about 14 carbon atoms, alkenyl or aralkyl having from 7 to about 14 carbon atoms, alkylene having from 2 to about 7 carbon atoms, and $R_1$ and $R_2$ or $R_3$ and $R_4$ in combination with each other represent cycloalkyl having from 5 to about 14 carbon atoms; $R_5$ and $R_6$ are the same as $R_1$–$R_4$ hereinabove and additionally may be hydrogen; and A is piperidinyl, morpholinyl, dialkylamino or alkylamino having from 2 to about 12 carbon atoms.

2. A composition of claim 1 wherein said stabilizer compound has the formula

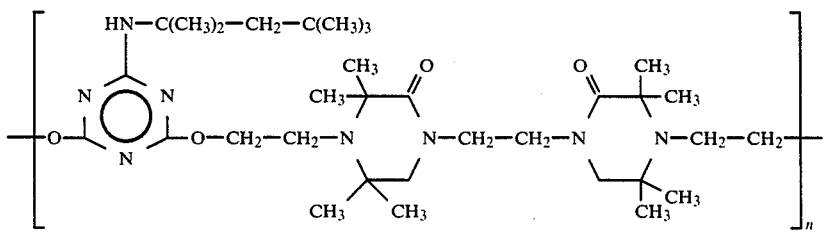

wherein n ranges from 2 to about 20.

3. A composition of claim 1 wherein said stabilizer compound has the formula
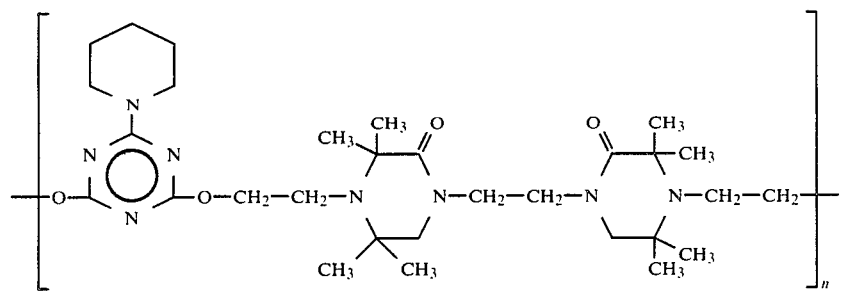
wherein n ranges from 2 to about 20.
4. A composition of claim 1 wherein said organic material is a polyolefin.
5. A composition of claim 4 wherein said organic material is selected from the group consisting of polypropylene, polyethylene and polyvinyl chloride.
* * * * *